United States Patent
Smith

(10) Patent No.: US 7,354,263 B2
(45) Date of Patent: Apr. 8, 2008

(54) MULTI DENTAL FLASK SYSTEM

(76) Inventor: Avis J. Smith, 87-10 149th Ave. - #2D, Howard Beach, NY (US) 11414

( * ) Notice: Subject to any disclaimer, the term of this patent is extended or adjusted under 35 U.S.C. 154(b) by 294 days.

(21) Appl. No.: 11/205,876

(22) Filed: Aug. 17, 2005

(65) Prior Publication Data
US 2007/0042073 A1    Feb. 22, 2007

(51) Int. Cl.
B28B 1/00      (2006.01)
A61C 13/00    (2006.01)

(52) U.S. Cl. ............ 425/179; 425/175; 425/176; 425/DIG. 11; 264/16; 433/34

(58) Field of Classification Search .......... 425/175, 425/176, 179, 180, 177, 178, 234, DIG. 11; 249/119, 120, 126; 264/16, 17, 18, 19, 20; 433/34
See application file for complete search history.

(56) References Cited

U.S. PATENT DOCUMENTS

| | | | | |
|---|---|---|---|---|
| 162,128 | A * | 4/1875 | White | 425/175 |
| 1,699,932 | A * | 1/1929 | Underdahl | 425/171 |
| 1,871,137 | A * | 8/1932 | Underdahl | 425/175 |
| 2,505,669 | A * | 4/1950 | Gottlieb | 425/178 |
| 3,635,630 | A * | 1/1972 | Greene | 425/175 |
| 3,988,094 | A * | 10/1976 | McGowan et al. | 425/175 |
| 4,546,261 | A * | 10/1985 | Gonser et al. | 250/492.1 |
| 4,839,521 | A * | 6/1989 | Oppawsky | 250/453.11 |
| 5,338,192 | A * | 8/1994 | Weber | 433/34 |
| 5,962,038 | A * | 10/1999 | Purvis et al. | 425/195 |
| 7,144,240 | B2 * | 12/2006 | Maravilla | 425/178 |

* cited by examiner

Primary Examiner—Yogendra Gupta
Assistant Examiner—Maria Veronica Ewald
(74) Attorney, Agent, or Firm—Charles E. Baxley

(57) ABSTRACT

A multi dental flask system. The system includes a boot, at least two dental flasks, a sleeve, and a wrench. The boot is affixed to a surface. The at least two dental flasks are stacked one on top of the other. A lowermost dental flask of the at least two dental flasks is non-rotatably received in the boot. The sleeve is replaceably affixed to the lowermost dental flask of the at least two dental flasks and houses the other at least one dental flask of the at least two dental flasks so as to allow the at least two dental flasks to be processed simultaneously. The wrench receives the sleeve and replaceably affixes the sleeve to the lowermost dental flask.

8 Claims, 4 Drawing Sheets

MULTI DENTAL FLASK SYSTEM

BACKGROUND OF THE INVENTION

1. Field of the Invention

The present invention relates to a dental flask system, and more particularly, the present invention relates to a multi dental flask system.

2. Description of the Prior Art

It is generally desired to form dentures of plastic, and for this result it is necessary to use heat in the process. For example, when acrylic plastic is used, a curing step is required for the polymerization of the plastic. This takes place after the acrylic plastic has been formed into the specific shape of the denture and placed into a dental flask. Unfortunately, there is no system for processing multiple flasks simultaneously. Thus, there exists a need for a system for processing multiple dental flasks simultaneously.

Numerous innovations for dental flasks and related devices have been provided in the prior art. Even though these innovations may be suitable for the specific individual purposes to which they address, they each differ in structure and/or operation and/or purpose from the present invention in that they do not teach a system for processing multiple dental flasks simultaneously.

FOR EXAMPLE, U.S. Pat. No. 3,635,630 to Greene teaches an apparatus and method for forming dentures wherein plastic inserts are placed within metal flask members to hold a dental mold therein. Acrylic plastic is then inserted in place of the mold to form the denture within the plastic inserts. The inset unit is then removed from the metal flask and held by a plastic clamping apparatus and the plastic denture is then cured in an ultrahigh frequency oven.

ANOTHER EXAMPLE, U.S. Pat. No. 3,988,094 to McGowan et al. teaches a multi-section dental flask for denture-making which includes a pair of threaded, longitudinally shiftable pins received in stepped, communicating bores in the anterior region of the primary closure sections of the flask to permit selective movement of the pins between a position precluding significant relative movement of the flask sections and a position permitting limited degrees of such movement. The pins are shifted to their movement-locking positions during all preliminary operations of the denture-making process, and thereafter moved to their recessed positions in order to ensure accurate reproduction of the denture model by compensating for the characteristic expansion and contraction of the denture material during hardening thereof. In anther embodiment, a flask lid is utilized in conjunction with compression bolts for resiliently holding the resilient three-piece flask together during the curing process without the need for a separate spring to compress as has heretofore been required. The flask lid preferably includes a releasably secured metallic ejector block which facilitates dislodgement of the finished denture from the hardened investment material within the flask.

STILL ANOTHER EXAMPLE, U.S. Pat. No. 4,546,261 to Gonser et al. teaches an apparatus and method for providing light curing of dentures and like materials. The denture is preferably of a material which is hardened or polymerized when exposed to visible light. An array of light sources is provided relative to a rotatable platform on which the dentures are placed. Each light source provides a substantially collimated light beam directed to optimally intercept the rotating denture. There are preferably four such light sources. Each light source has a visible light bandpass characteristic and directed at an angle within 25°-45° of the platform surface. The light beams are directed at the platform surface in overlapping fashion so as to provide continuous incident light on the denture during each cycle of rotation.

YET ANOTHER EXAMPLE, U.S. Pat. No. 4,839,521 to Oppawsky teaches a treatment chamber as an accessory device for an illuminator for the photopolymerization of dental plastic. The chamber is both light-tight and has at least one movable chamber wall. A light conductor is provided for the light input.

STILL YET EXAMPLE, U.S. Pat. No. 5,338,192 to Weber teaches an expander for a three part, Hanau dental flask to add vertical height to the flask when the total height of the wax model of a prosthesis and mold material exceeds the normal height of the flask. The flask expander requires no alteration or modification of the standard dental flask, and sandwiches in between the existing flask base and body or between the flask body and lid.

It is apparent that numerous innovations for dental flasks and related devices have been provided in the prior art that are adapted to be used. Furthermore, even though these innovations may be suitable for the specific individual purposes to which they address, they would not be suitable for the purposes of the present invention as heretofore described because they do not teach a system for processing multiple dental flasks simultaneously.

SUMMARY OF THE INVENTION

ACCORDINGLY, AN OBJECT of the present invention is to provide a multi dental flask system that avoids the disadvantages of the prior art.

ANOTHER OBJECT of the present invention is to provide a multi dental flask system that is simple to use.

BRIEFLY STATED, STILL ANOTHER OBJECT of the present invention is to provide a multi dental flask system. The system includes a boot, at least two dental flasks, a sleeve, and a wrench. The boot is affixed to a surface. The at least two dental flasks are stacked one on top of the other. A lowermost dental flask of the at least two dental flasks is non-rotatably received in the boot. The sleeve is replaceably affixed to the lowermost dental flask of the at least two dental flasks and houses the other at least one dental flask of the at least two dental flasks so as to allow the at least two dental flasks to be processed simultaneously. The wrench receives the sleeve and replaceably affixes the sleeve to the lowermost dental flask.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows.

Figure 1:
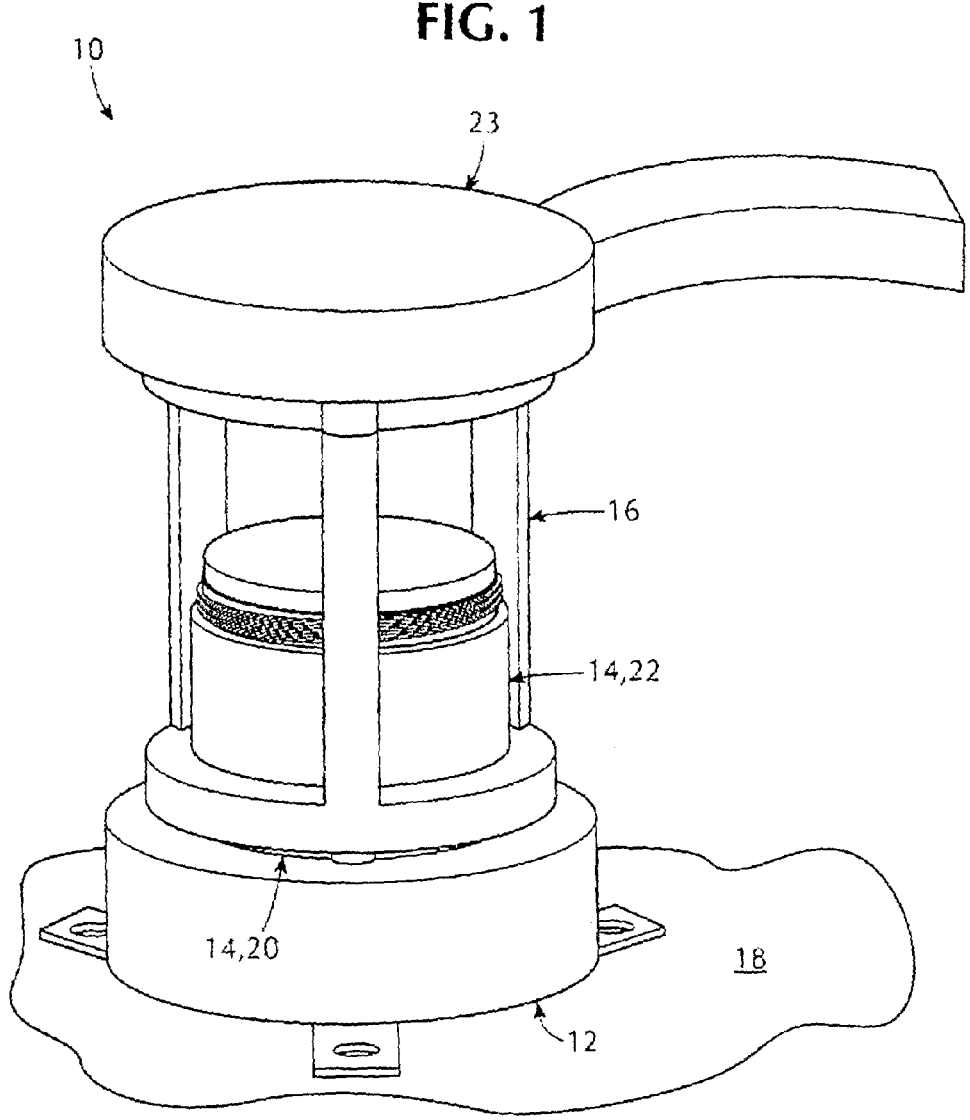
FIG. 1 is a diagrammatic perspective view of the multi dental flask system of the present invention.

LIST OF REFERENCE NUMERALS UTILIZED
IN THE DRAWING 10 multi dental flask system of present invention
12 boot for affixing to surface 18
14 at least two dental flasks
16 sleeve
18 surface
20 lowermost dental flask of at least two dental flasks 14
22 other at least one dental flask of at least two dental flasks 14
23 wrench
24 side wall of boot 12
26 plurality of attachments of boot 12 for affixing boot 12 to surface 18
28 plurality of tabs of plurality of attachments 26 of boot 12 for affixing boot 12 to surface 18
30 through bores in plurality of tabs 28 of plurality of attachments 26 of boot 12, respectively, for receiving screws or the like for affixing boot 12 to surface 18
32 interior surface of side wall 24 of boot 12
34 plurality of female portions in interior surface 32 of side wall 24 of boot 12
36 plurality of blind slots of plurality of female portions 34 in interior surface 32 of side wall 24 of boot 12
37 body of each dental flask of at least two dental flasks 14
38 side wall of body 37 of each dental flask of at least two dental flasks 14
39 open top of body 37 of each dental flask of at least two dental flasks 14
40 exterior surface of side wall 38 of body 37 of each dental flask of at least two dental flasks 14
42 plurality of male portions on exterior surface 40 of side wall 38 of body 37 of each dental flask of at least two dental flasks 14
43 plurality of protrusions of plurality of male portions 42 on exterior surface 40 of side wall 38 of body 37 of each dental flask of at least two dental flasks 14
44 threads on exterior surface 40 of side wall 38 of body 37 of each dental flask of at least two dental flasks 14
46 interior surface of side wall 38 of body 37 of each dental flask of at least two dental flasks 14
48 plurality of female portions in interior surface 46 of side wall 38 of body 37 of each dental flask of at least two dental flasks 14
50 plurality of blind slots of plurality of female portions 48 in interior surface 46 of side wall 38 of body 37 of each dental flask of at least two dental flasks 14
51 bottom of each dental flask of at least two dental flasks 14
52 lid of each dental flask of at least two dental flasks 14
53 knock-out disk of each dental flask of at least two dental flasks 14 for facilitating removal of contents of associated dental flask of at least two dental flasks 14
54 plurality of male portions of lid 52 of each dental flask of at least two dental flasks 14
56 plurality of tabs of plurality of male portions 54 of lid 52 of each dental flask of at least two dental flasks 14
58 lower ring of sleeve 16
60 upper disk of sleeve 16
62 plurality of ribs of sleeve 16
64 interior surface of lower ring 58 of sleeve 16
66 threads on interior surface 64 of lower ring 58 of sleeve 16
68 plurality of protrusions on upper disk 60 of sleeve 16
70 body of wrench 23
72 handle of wrench 23
74 side wall of body 70 of wrench 23
75 open bottom of body 70 of wrench 23
76 interior surface of side wall 74 of body 70 of wrench 23
78 plurality of female portions in interior surface 76 of side wall 74 of body 70 of wrench 23
80 plurality of blind slots of plurality of female portions 78 in interior surface 76 of side wall 74 of body 70 of wrench 23

DETAILED DESCRIPTION OF THE
PREFERRED EMBODIMENT

Figure 2:
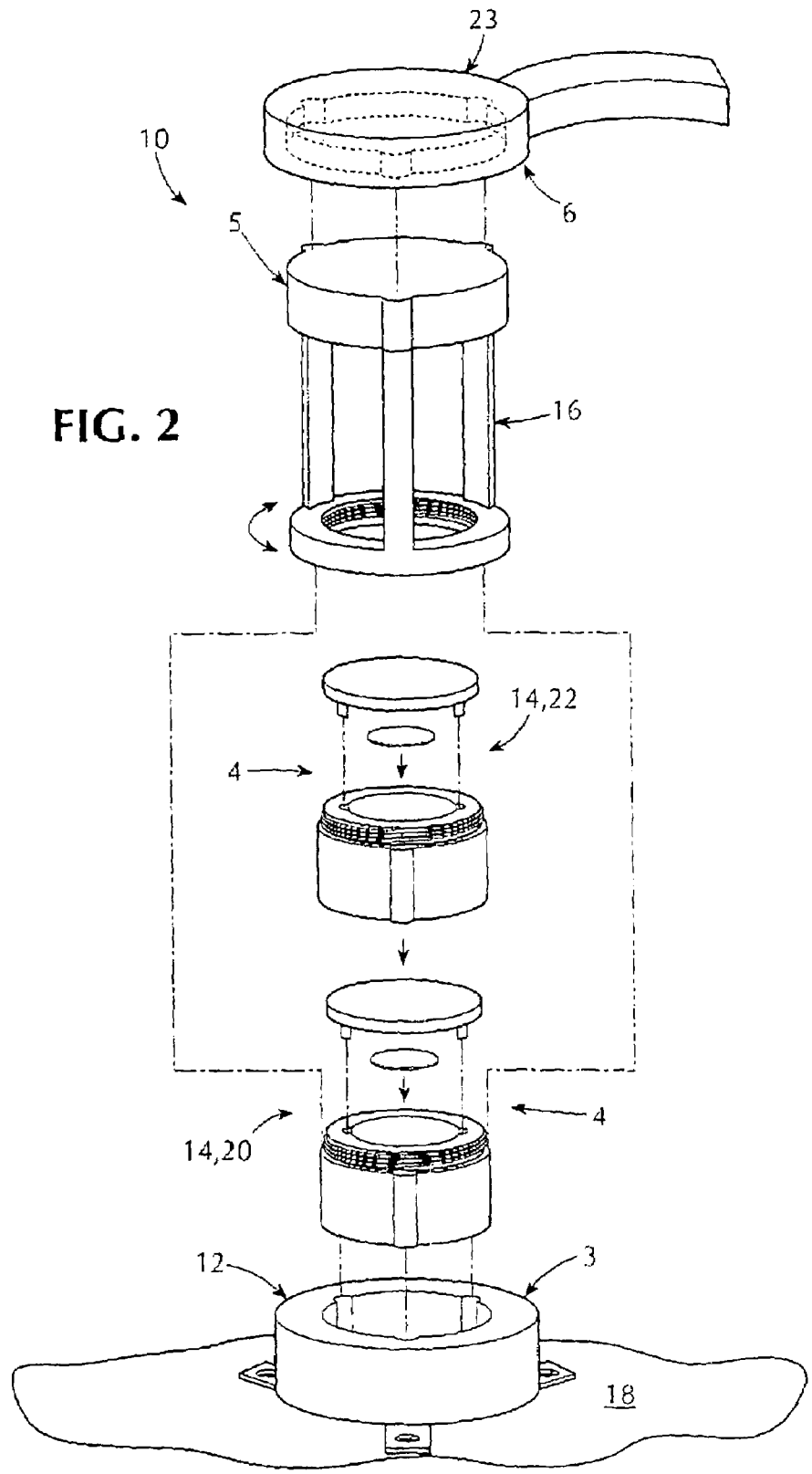
FIG. 2 is an exploded diagrammatic perspective view of the multi dental flask system of the present invention shown in FIG. 1.

Referring now to the figures, in which like numerals indicate like parts, and particularly to FIGS. 1 and 2, which are, respectively, a diagrammatic perspective view of the multi dental flask system of the present invention, and, an exploded diagrammatic perspective view of the multi dental flask system of the present invention shown in FIG. 1, the multi dental flask system of the present invention is shown generally at 10.

The multi dental flask system 10 comprises a boot 12, at least two dental flasks 14, and a sleeve 16. The boot 12 is for affixing to a surface 18. The at least two dental flasks 14 are stacked one on top of the other, with a lowermost dental flask 20 being non-rotatably received in the boot 12. The sleeve 16 is replaceably affixed to the lowermost dental flask 20 and houses the other at least one dental flask 22 so as to allow the at least two dental flasks 14 to be processed simultaneously.

The multi dental flask system 10 further comprises a wrench 23. The wrench 23 receives the sleeve 16, and replaceably affixes the sleeve 16 to the lowermost dental flask 20.

Figure 3:
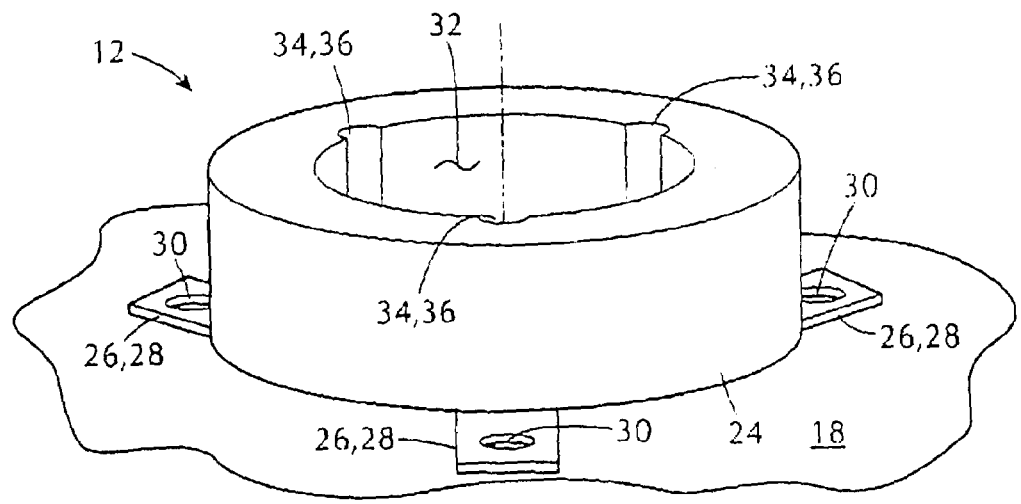
FIG. 3 is an enlarged diagrammatic perspective view of the boot of the multi dental flask system of the present invention identified by ARROW 3 in FIG. 2.

The specific configuration of the boot 12 can best be seen in FIG. 3, which is an enlarged diagrammatic perspective view of the boot of the multi dental flask system of the present invention identified by ARROW 3 in FIG. 2, and as such, will be discussed with reference thereto.

The boot 12 is cupped-shaped so as to be able to receive the lowermost dental flask 20, and has a side wall 24 and a plurality of attachments 26 for affixing the boot 12 to the surface 18. The plurality of attachments 26 of the boot 12 are preferably a plurality of tabs 28, numbering preferably three, extending radially outwardly from the boot 12, and having through bores 30 therethrough, respectively, for receiving screws or the like for affixing the boot 12 to the surface 18. The plurality of tabs 28 of the boot 12 are horizontally-oriented and spaced-apart from each other, preferably equally.

The side wall 24 of the boot 12 is vertically-oriented and has an interior surface 32. The interior surface 32 of the side wall 24 of the boot 12 is provided with a plurality of female portions 34, preferably a plurality of blind slots 36, numbering preferably two. The plurality of blind slots 36 in the side wall 24 of the boot 12 are vertically-oriented and spaced-apart from each other, preferably equally.

Figure 4:
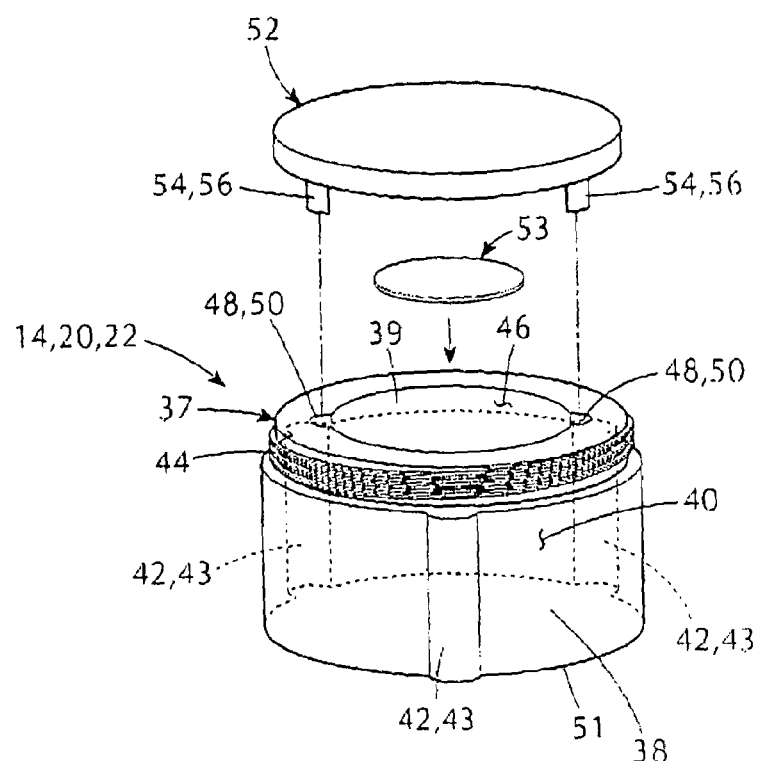
FIG. 4 is an enlarged diagrammatic perspective view of a dental flask of the multi dental flask system of the present invention identified by ARROWS 4 in FIG. 2.

The specific configuration of each dental flask 14 can best be seen in FIG. 4, which is an enlarged diagrammatic perspective view of the dental flask of the multi dental flask system of the present invention identified by ARROWS 4 in FIG. 2, and as such, will be discussed with reference thereto.

Each dental flask 14 is cupped-shaped and has a body 37 with a side wall 38 defining an open top 39. The side wall 38 of the body 37 of each dental flask 14 is vertically-oriented and has an exterior surface 40. The exterior surface 40 of the side wall 38 of the body 37 of each dental flask 14 is provided with a plurality of male portions 42, preferably a plurality of protrusions 43, preferably numbering three. The plurality of protrusions 43 on the side wall 38 of the body 37 of each dental flask 14 are vertically-oriented, spaced-apart form each other, preferably equally, and cooperate with the plurality of blind slots 36 in the side wall 24 of the boot 12, respectively, so as to allow the lowermost dental flask 20 to be non-rotatably received in the boot 12.

The exterior surface 40 of the side wall 38 of the body 37 of each dental flask 14 is further provided with threads 44. The threads 44 on the body 37 of each dental flask 14 extend therearound and are disposed above the plurality of protrusions 43 on the side wall 38 of the body 37 of an associated dental flask 14.

The side wall 38 of the body 37 of each dental flask 14 further has an interior surface 46. The interior surface 46 of the side wall 38 of the body 37 of each dental flask 14 is provided with a plurality of female portions 48, preferably a plurality of blind slots 50, numbering preferably two. The plurality of blind slots 50 in the side wall 38 of the body 37 of each dental flask 14 are vertically-oriented, spaced-apart form each other, preferably equally, and depend from the open top 39 of the body 37 of an associated dental flask 14.

Each dental flask 14 further has a bottom 51 and a knock-out disk 53. The knock-out disk 53 of each dental flask 14 sits in an associated dental flask 14, on the bottom 51 of the associated dental flask 14, for facilitating removal of contents of the associated dental flask 14.

Each dental flask 14 further has a lid 52. The lid 52 of each dental flask 14 selectively closes the open top 39 of the body 37 of an associated dental flask 14.

The lid 52 of each dental flask 14 is provided with a plurality of male portions 54, preferably a plurality of tabs 56, preferably numbering two. The plurality of tabs 56 on the lid 52 of each dental flask 14 depend vertically therefrom, are spaced-apart form each other, preferably equally, and cooperate with the plurality of blind slots 50 in the side wall 38 of the body 37 of an associated dental flask 14, respectively, so as to allow the lid 52 of each dental flask 14 to be non-rotatably received by the body 37 of an associated dental flask 14.

Figure 5:
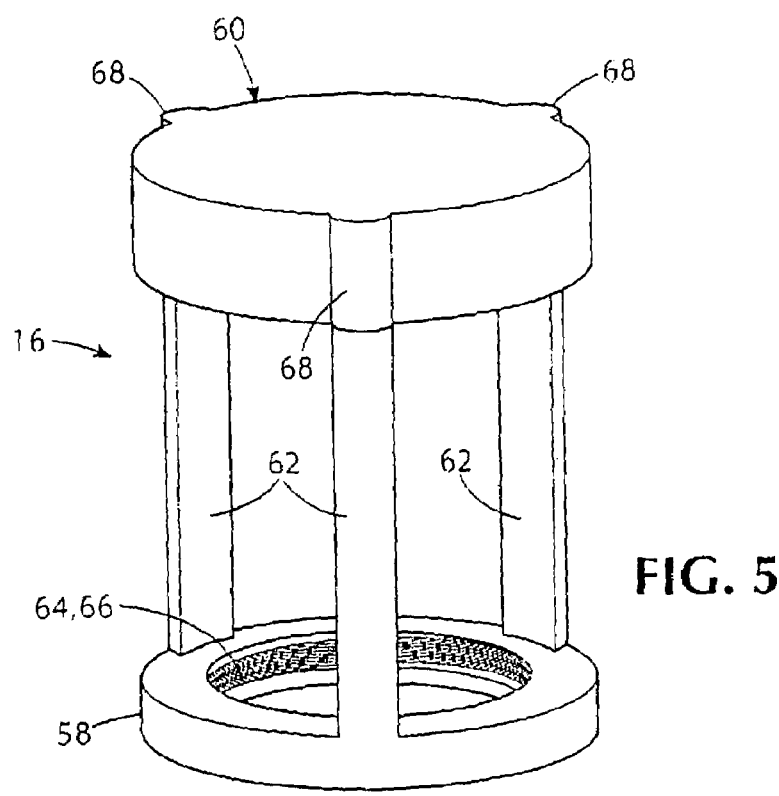
FIG. 5 is an enlarged diagrammatic perspective view of the sleeve of the multi dental flask system of the present invention identified by ARROW 5 in FIG. 2.

The specific configuration of the sleeve 16 can best be seen in FIG. 5, which is an enlarged diagrammatic perspective view of the sleeve of the multi dental flask system of the present invention identified by ARROW 5 in FIG. 2, and as such, will be discussed with reference thereto. The sleeve 16 is generally cylindrically-shaped and has a lower ring 58, an upper disk 60, and a plurality of ribs 62. The upper disk 60 of the sleeve 16 is spaced above the lower ring 58 of the sleeve 16 and is connected thereto by the plurality of ribs 62 of the sleeve 16. The lower ring 58 of the sleeve 16 and the upper disk 58 of the sleeve 16 are horizontally-oriented and the plurality of ribs 62 of the sleeve 16 are vertically-oriented, preferably three in number, and spaced-apart form each other, preferably equally. The lower ring 58 of the sleeve 16 has an interior surface 64. The interior surface 64 of the lower ring 58 of the sleeve 16 is provided with threads 66. The threads 66 on the lower ring 58 of the sleeve 16 extend therearound and threadably engage the threads 44 on the body 37 of the lowermost flask 20 so as to allow the other at least one dental flask 22 that is stacked on the lowermost dental flask 20 to be housed in the sleeve 16, between the ribs 62 thereof, so as to allow the at least two dental flasks 14 to be processed simultaneously.

The upper disk 60 of the sleeve 16 is provided with a plurality of protrusions 68. The plurality of protrusions 68 of the sleeve 16, preferably three in number, extend radially outwardly therefrom, and are spaced therearound, preferably equally.

Figure 6:
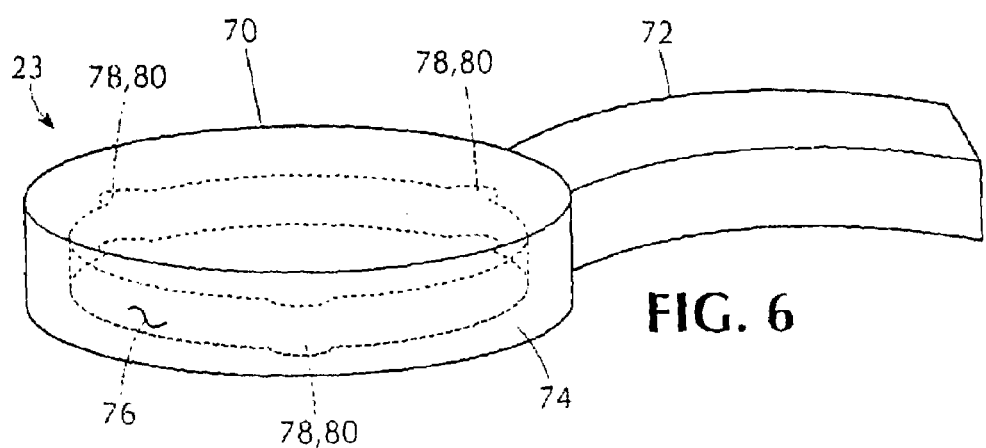
FIG. 6 is an enlarged diagrammatic perspective view of the wrench of the multi dental flask system of the present invention identified by ARROW 6 in FIG. 2.

The specific configuration of the wrench 23 can best be seen in FIG. 6, which is an enlarged diagrammatic perspective view of the wrench of the multi dental flask system of the present invention identified by ARROW 6 in FIG. 2, and as such, will be discussed with reference thereto.

The wrench 23 has a body 70 and a handle 72. The handle 72 of the wrench 23 extends radially outwardly from the body 70 of the wrench 23.

The body 70 of the wrench 23 is inverted cup-shaped defined by a side wall 74 having an open bottom 75, is horizontally-oriented, and replaceably receives the upper disk 60 of the sleeve 16 to rotate therewith.

The side wall 74 of the body 70 of the wrench 23 has an interior surface 76. The interior surface 76 of the side wall 74 of the body 70 of the wrench 23 is provided with a plurality of female portions 78, preferably a plurality of blind slots 80, numbering preferably three. The plurality of blind slots 80 in the side wall 74 of the body 74 of the wrench 23 are vertically-oriented, spaced-apart form each other, preferably equally, extend from the open bottom 75 of the body 70 of the wrench 23, and cooperate with the plurality of protrusions 68 of the sleeve 16, respectively, so as to allow the wrench 23 to non-rotatably receive the sleeve 16 and rotate therewith to thread and unthread the sleeve 16 onto and off of the lowermost dental flask 20.

It will be understood that each of the elements described above, or two or more together, may also find a useful application in other types of constructions differing from the types described above.

While the invention has been illustrated and described as embodied in a multi dental flask system, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A multi dental flask system, comprising:
a) a boot;
b) at least two dental flasks; and
c) a sleeve;
wherein said boot is for affixing to a surface;
wherein said at least two dental flasks are stacked one on top of the other;
wherein a lowermost dental flask of said at least two dental flasks is non-rotatably received in said boot;

wherein said sleeve is replaceably affixed to said lowermost dental flask of said at least two dental flasks; and wherein said sleeve houses the other at least one dental flask of said at least two dental flasks so as to allow said at least two dental flasks to be processed simultaneously, wherein said boot has a side wall;

wherein said side wall of said boot has an interior surface; and wherein said interior surface of said side wall of said boot is provided with a plurality of blind slots, wherein each dental flask has a body;

wherein said body of each dental flask has an exterior surface;

wherein said exterior surface of said body of each dental flask is provided with a plurality of protrusions; and wherein said plurality of protrusions of said body of each dental flask cooperate with said plurality of blind slots in said boot, respectively, so as to allow said lowermost dental flask to be non-rotarably received in said boot, wherein said exterior surface of said body of each dental flask is provided with threads;

wherein said threads on said body of each dental flask extend therearound; and wherein said threads on said body of each dental flask are disposed above said plurality of protrusions on said side wall of said body of an associated dental flask.

2. The system as defined in claim 1, wherein said side wall of said body of each dental flask has an interior surface; and wherein said interior surface of said side wall of said body of each dental flask is provided with a plurality of blind slots.

3. The system as defined in claim 2, wherein said lid of each dental flask is provided with a plurality of tabs;

wherein said plurality of tabs of said lid of each dental flask depend therefrom; and wherein said plurality of tabs of said lid of each dental flask cooperate with said plurality of blind slots in said body of an associated dental flask, respectively, so as to allow said lid of each dental flask to be non-rotatably received by said body of an associated dental flask.

4. The system as defined in claim 1, wherein said sleeve has a lower ring;

wherein said sleeve has an upper disk;

wherein said sleeve has a plurality of ribs;

wherein said upper disk of said sleeve is spaced above said lower ring of said sleeve; and wherein said upper disk of said sleeve is connected to said lower ring of said sleeve by said plurality of ribs of said sleeve.

5. The system as defined in claim 4, wherein said lower ring of said sleeve has an interior surface;

wherein said interior surface of said lower ring of said sleeve is provided with threads;

wherein said threads of said lower ring of said sleeve extend therearound; and wherein said threads of said lower ring of said sleeve threadably engage said threads of said body of said lowermost flask so as to allow said other at least one dental flask that is stacked on said lowermost dental flask to be housed in said sleeve, between said ribs thereof, so as to allow said at least two dental flasks to be processed simultaneously.

6. The system as defined in claim 4, wherein said upper disk of said sleeve is provided with a plurality of protrusions; and wherein said plurality of protrusions of said sleeve extend radially outwardly therefrom.

7. The system as defined in claim 6, wherein said wrench has a body;

wherein said wrench has a handle;

wherein said handle of said wrench extends radially outwardly from said body of said wrench; and wherein said body of said wrench replaceably receives said upper disk of said sleeve to rotate therewith.

8. The system as defined in claim 7, wherein said body of said wrench has a side wall;

wherein said side wall of said body of said wrench has an interior surface;

wherein said interior surface of said side wall of said body of said wrench is provided with a plurality of blind slots; and wherein said plurality of blind slots in said body of said wrench cooperate with said plurality of protrusions of said sleeve, respectively, so as to allow said wrench to non-rotatably receive said sleeve and rotate therewith to thread and unthread said sleeve onto and off of said lowermost dental flask.

* * * * *